United States Patent [19]

Jermyn

[11] Patent Number: 5,655,686
[45] Date of Patent: Aug. 12, 1997

[54] DEVICE FOR UNIDIRECTIONALLY DISPENSING A HYGIENIC CLEANING LIQUID

[76] Inventor: Arthur Charles Jermyn, 15914 Overview Rd., Poway, Calif. 92064

[21] Appl. No.: 454,432

[22] Filed: May 30, 1995

[51] Int. Cl.$^6$ .................................................. B65D 37/00
[52] U.S. Cl. .......................... 222/211; 222/212; 222/422; 222/481.5; 222/494
[58] Field of Search ................................. 222/211, 212, 222/422, 481.5, 494

[56] References Cited

U.S. PATENT DOCUMENTS

| | | | |
|---|---|---|---|
| 4,122,979 | 10/1978 | Laauwe | 222/211 X |
| 4,340,157 | 7/1982 | Darner | 222/212 X |
| 4,568,004 | 2/1986 | Goncalves | 222/212 X |
| 5,033,654 | 7/1991 | Bennett | 222/211 X |
| 5,079,013 | 1/1992 | Belanger | 222/481.5 X |
| 5,366,115 | 11/1994 | Kersten et al. | 222/212 X |

*Primary Examiner*—Joseph Kaufman

[57] ABSTRACT

The invention relates to a device for unidirectionally dispensing a hygienic cleaning and/or flushing liquid into the nasal and sinus cavities when an occluder is inserted into one of the nostrils. The liquid is contained in a pliable container which, upon insertion of the occluder into one of the nostrils and deformation of the container per se by squeezing, will cause the liquid to move via a passageway to the occluder and into the nostril. The device is provided with an anti-retractive valve which permits a unidirectional flow of the liquid only in a dispensing direction so any contaminated liquid that had been previously dispensed cannot reenter the container through the liquid dispensing passageway.

3 Claims, 2 Drawing Sheets

DEVICE FOR UNIDIRECTIONALLY DISPENSING A HYGIENIC CLEANING LIQUID

FIELD OF THE INVENTION

The invention relates to a dispenser, and more particularly, to a device for dispensing a hygienic liquid into the nasal and sinus cavities for cleansing and flushing. In addition, the device is one which will dispense only in a unidirectional path, dispensing only the liquid within the receptacle and not permitting any contaminated liquid to re-enter the receptacle for further dispensing.

DESCRIPTION OF THE ART

Although there are many types of spray devices utilized for use with respect to the nose for spraying the nasal and sinus cavities, there is none which will prevent a return of any contaminated liquid to the receptacle. The liquid usually sprayed into the nose runs out and carries germs and residue therewith, which can re-enter the receptacle via the spray tip within the nostril, thereby contaminating the liquid within the receptacle. This return of the liquid already dispensed from the receptacle results in the liquid being a contaminate rather than an hygienic liquid. There is also no way in which the present dispensers can be washed or disinfected so the liquid is always certain to be hygienic with no contamination. Consequently, it can be said that the devices currently in use as a spray dispensing device in no way permits the hygienic liquid to be protected against re-contamination. In the device disclosed hereinafter all parts of the system are easily removable for cleaning and disinfecting and/or sterilizing. The nasal occluder is easily removed following each use and can be washed and dried for subsequent use. Other features are noted hereinafter which will distinguish the advantages of the present device as compared to those now in use. Clearly, the components of the device composing the invention are such that in combination they provide for a leak-proof device that can be readily utilized under most any conditions.

SUMMARY OF THE INVENTION

The present invention is concerned with a device for hygienically cleaning and flushing the nasal and sinus passages with a liquid contained in a pliant receptacle having an open end. An intermediate member is releasably attached to the receptacle at its open end for closing and sealing the end and into which an occluder can also be releasably attached at the other end, the occluder being readily insertable into one of the nostrils of the nose. The receptacle, per se, is of a pliant plastic material which permits the user to squeeze the bottle in order to eject and provide a flow of the liquid from the receptacle through the intermediate member, through the occluder and into the nose. Control means associated with either the intermediate member or the occluder permits and maintains a flow of the liquid only as long as the pliant receptacle is deformed and only in a direction to discharge the liquid from the occluder to the nostril.

The intermediate member is provided with a liquid passageway extending from one end of the member within the receptacle to the other end without the intermediate member. A second liquid passageway in the occluder is co-extensive with that of the intermediate member and directs the liquid to the nostril in which the occluder has been inserted. In the passageway of either the intermediate member or the occluder an anti-retractive device is inserted to control the direction of flow of the liquid from the receptacle to the nostril when the plaint receptacle is deformed by squeezing. With such a control member, the liquid flows unidirectionally to the occluder and hence to the nostril. Upon release of the pressure applied to the receptacle, the receptacle returns to its original state by the entry of air into the receptacle through a breathing hole in which there is also an anti-retractive device or check valve. With the entry of air into the receptacle via the check valve, the air pressure within the receptacle becomes the same as the atmospheric pressure outside of the receptacle. In this way, the receptacle quickly returns to its original shape and is immediately ready for another deformation to dispense another stream of liquid without sucking in any of the already dispensed liquid. It has been found that with a device of this type which can be readily disassembled for cleaning and disinfecting, a health standard is acquired that is not heretofore possible with other types of dispensers utilized for the same purpose.

SUMMARY OF THE INVENTION

The primary object of the invention is to provide a device for hygienically cleaning and flushing the nasal and sinus passages with a liquid contained in a pliant receptacle and having a unidirectional flow.

A further object of the invention is to provide a liquid dispensing device in which the elements of the device can be readily disassembled, cleaned and disinfected for future use and which, when used, alleviates any possibility of contamination of the hygienic liquid in the receptacle by any liquid already dispensed.

Another object of the invention is to provide a liquid dispensing device in which the pressure within the receptacle for the hygienic liquid is always at a level with that of the atmospheric pressure to guarantee a unidirectional flow of the liquid upon deformation of the pliant receptacle.

Still another object of the invention is to provide a liquid dispensing device for hygienically cleaning and flushing the nasal and sinus passages with a liquid contained in a pliant receptacle in which a minimum number of parts are utilized and which permits easy disassembling of the device for cleaning and disinfecting, and/or sterilizing after each use.

These and other objects and advantages of the invention will be apparent to those skilled in the art by the description which follows.

DESCRIPTION OF THE DRAWINGS

Reference is now made to the accompanying drawings wherein like reference numerals and characters designate like parts and wherein.

DESCRIPTION OF PREFERRED EMBODIMENTS

Figure 1:
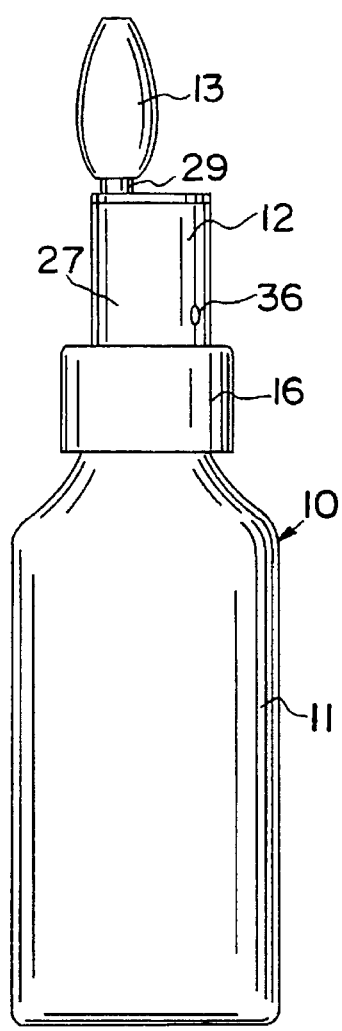
FIG. 1 is an elevational view of a liquid dispenser in accordance with the invention and incorporating the elements required to provide a dispenser which is capable of a unidirectional flow of the liquid contained therein.

With respect to FIG. 1 in particular, the device 10, according to the invention, comprises a pliant receptacle 11, an intermediate member 12 and an occluder 13. These are the primary elements, each of which will be defined and described in more detail hereinafter.

The receptacle 11 is preferably a very pliant plastic material which can be readily deformed upon squeezing so as to move or flush a liquid within the receptacle toward the intermediate member 12 and the occluder 13. As is well known, such a receptacle can take the form of a bottle or similar shape with an open end 14 that is provided with a threaded portion 15 for receiving a cap 16.

Figure 2:
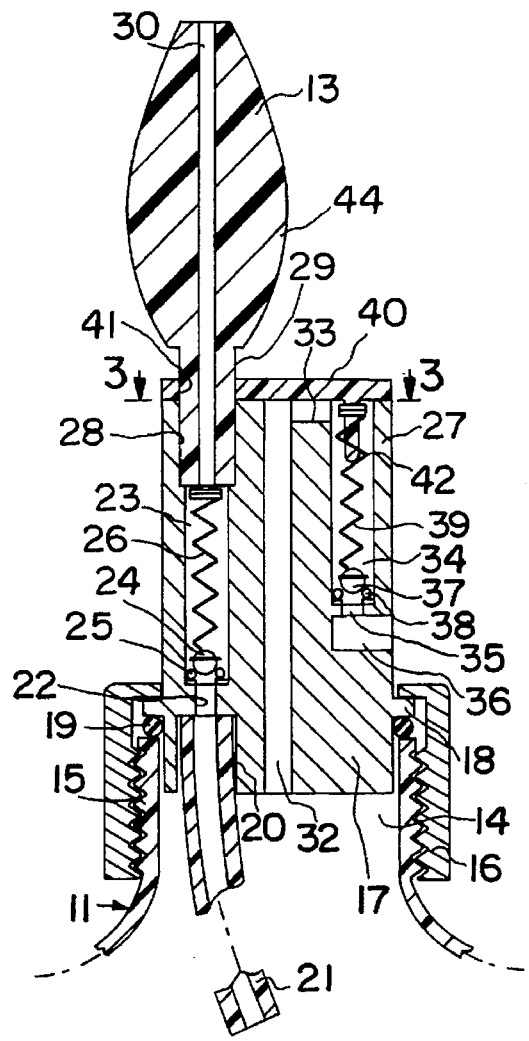
FIG. 2 is a vertical section through the elements attached to and forming a part of the dispenser associated with the open end thereof for sealing the end and for providing a unidirectional flow of the liquid.
Figure 3:
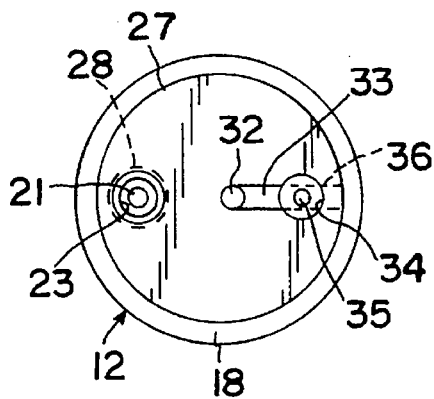
FIG. 3 is a plan view of the intermediate member taken substantially along the line 3—3 of FIG. 2 and showing the elements comprising the liquid and the air passageways for maintaining the receptacle at a pressure uniform with that of the atmosphere.

The intermediate member 12 is shown in more detail in FIG. 2. In this disclosure the member 12 comprises a portion 17 which extends into the open end 14 of the receptacle and is provided with a shoulder 18 for engaging an O-ring 19 arranged between the shoulder and the end of the threaded portion 15 of the receptacle 11. As shown in this FIG. 2, the cap 16 upon being threaded onto the portion 15 compresses the O-ring 19 between the neck of the bottle and the shoulder 18 to seal the receptacle thereby providing a closure which prevents any leakage of the liquid within the receptacle. Also, the portion 17 is provided with a counterbore 20 for receiving an end of a plastic tube 21 that extends into the liquid within the receptacle for directing the liquid to the intermediate member 12. In connection with the counterbore 20, a small aperture 22 connects the counterbore 20 to a chamber 23 in which there is arranged a stainless steel ball 24 which is seated against a small O-ring 25 within the chamber and adjacent to the aperture 22 by a spring 26. The end 27 of the member 12 that is without the open end 14 of the receptacle 11 is provided with a counterbore 28 that is coextensive with counterbore 20, aperture 22 and chamber 23 for receiving the extension 29 of the occluder 13. The occluder 13 is provided with a central aperture 30 that is coextensive with the chamber 23 when the extension 29 is inserted in the counterbore 28, thereby providing an exit for the liquid from the other end of the chamber 23.

Also associated with the intermediate member 12 is a vertical opening 32 which provides a passageway for air via a slot 33 between opening 32 and a chamber 34. The chamber 34 is connected via an aperture 35 to an air entry opening 36. With this arrangement, this series of opening 36, aperture 35, chamber 34, slot 33, and the vertical opening 32 provide an air passageway connecting the atmosphere with the interior of the receptacle 11. In the chamber 34, as in chamber 23, there is also arranged a ball 37 which, as previously described with respect to the chamber 23, is biased against an O-ring 38 by spring 39 to provide a cut-off of any air flow from the atmosphere to the interior of the receptacle under normal conditions. It will be noted that the outer end of the intermediate member 12 carries a plate 40 having an aperture 41 for permitting the extension 29 of the occluder 13 to be inserted in the counterbore 28. The plate 40 seals the end of member 12 and can be provided with an extension or nib 42 for engaging and/or centering the spring 39 within the chamber 34. With the arrangement of the springs 26, 39 and balls 24, 37 within the respective chambers 23 and 34 an anti-retractive check valve is provided in each of the liquid and air passageways.

The occluder 13 is of a shape and size to permit entry of the bulb-shaped portion 44 into the nostril so the liquid dispensed from the receptacle can be forced or circulated into the nasal and sinus cavities. The liquid passageway 30 of the occluder 13 is coextensive with chamber 23 and is shown as terminating in a single aperture at the very end of portion 44. As an alternative a series of small holes can be provided so that a flow in the form of a spray can be utilized rather than a direct stream as shown in FIG. 2.

In the operation of the device 10, the receptacle is first filled with a saline solution or a prescribed liquid for cleansing and flushing the sinus and nasal cavities. The intermediate member is then inserted in the open end 14 of the receptacle 11, thereby sealing the open end when the cap 16 seats the shoulder 18 of the intermediate member against the O-ring 19. A liquid passageway to the occluder is then provided but only when the receptacle is squeezed to deform the latter, thereby forcing the liquid through the tube 21 into aperture 22 and against the ball 24 to raise it away from the O-ring 25. The liquid moves from the chamber 23 and then into the liquid passageway 30 of the occluder 13 and is finally dispensed from the end of the passageway 30 into the nostril in which the portion 44 has been inserted. The dispensing occurs as soon as squeezing of the receptacle takes place and will continue so long as squeezing is possible.

When the pressure due to squeezing is removed from the pliant receptacle 11 it can return to its normal position only when the air forced out of the receptacle by squeezing can be replaced by air from the outside of the receptacle so that an air pressure differential no longer exists between the inside and outside of the receptacle 11. This pressure release takes place immediately thereby causing spring 26 to return ball 24 into engagement with O-ring to prevent any further dispensing of the liquid. Further, as the pressure release takes place, the pressure differential between that inside and that outside the receptacle 11 is equalized. This is due to the outside pressure via the air entry opening 36 and aperture 35 causing ball 37 to disengage from O-ring 38, thereby permitting air to enter receptacle 11 to establish an equalization of pressure. Once the pressure has been equalized, the ball 37 assumes its normal position closing the aperture 35 in view of the force exerted thereagainst by the spring 39. Hence, with the balls 29 and 37 in their sealing positions there is no possibility of any dispensed liquid reentering the receptacle 11 to contaminate the liquid not yet dispensed.

Figure 4:
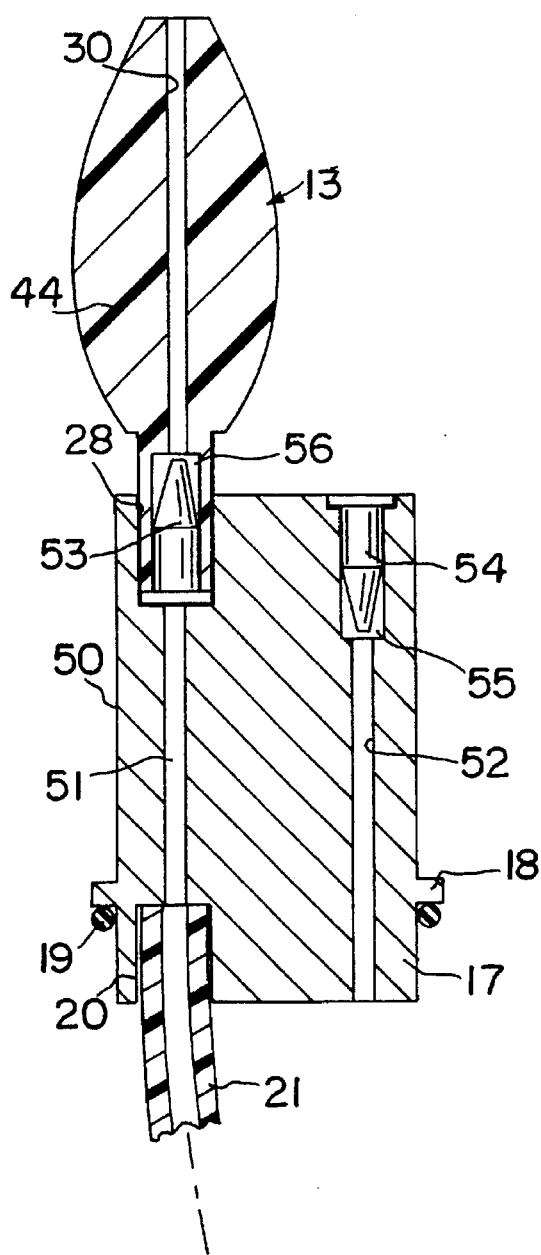
FIG. 4 is a vertical section through the intermediate member and similar to that shown in FIG. 2 for disclosing another embodiment of the invention with a different type of anti-retractive check valve.
Figure 5:
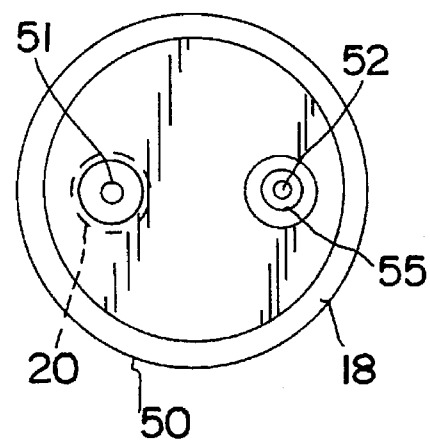
FIG. 5 is a plan view of the intermediate member showing primarily the arrangement of a different relation of the liquid and air passageways in the intermediate member for use with a different type of anti-retractive check valves.

Reference is now made to FIG. 4 in which another embodiment of the invention is disclosed and described. In this arrangement the intermediate member 50 is provided with two (2) passageways, the first being the liquid passageway 51 and the second being the air passageway 52 which is used to equalize the air pressure between the atmosphere and the inside of the receptacle 11. The structure for securing the intermediate member 50 to the open end 14 of the receptacle 11 is the same as that described hereinabove. However, in place of spring biased balls for controlling the opening or closing of the passageways a commercially available check valve is utilized. The check valve 53 as shown in FIG. 4, is arranged within the extension 29 of the occluder 13 rather than in the intermediate member 12 and the check valve 54 for controlling the entrance or equalization of the air pressure between the inside and outside of the receptacle 11 is inserted and sealed in the counterbore 55 in the end of the air passageway 52. Alternatively, the check valve 54 can be contained by a plate, as shown in FIG. 2 having only a hole in alinement with the liquid passageway 51 for receiving the extension 29 of the occluder 13.

The check valve 53 is shown in FIG. 4 as being arranged in a counterbore 56 in the extension 29 of the occluder 13 and coextensive with the liquid passageway 51 and the counterbore 20. The check valve 53 seals the liquid within the receptacle 11 and prevents any flow of the liquid until the pliant receptacle 11 has again be squeezed to dispense the liquid.

Figure 6:
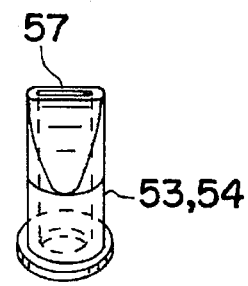
FIG. 6 is a perspective view of an anti-retractive check valve such as shown in FIG. 4, in which the valve assumes a closed position when there is no pressure difference on the two sides of the valve.
Figure 7:
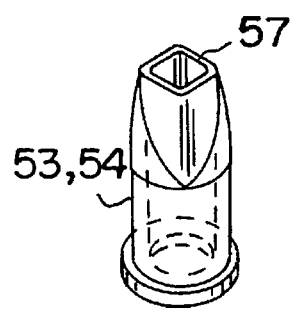
FIG. 7 is a perspective view similar to FIG. 6 showing the way in which the anti-retractive check valve opens when a pressure difference is induced on the two sides of the valve.

In FIGS. 6 and 7 the check valves as designated by 53 and 54 hereinabove, is shown in the positions assumed when arranged in the intermediate member 50, as shown in FIG. 4. The valve is made of a very soft polyethylene material and is commercially available for use in small apertures or openings. In FIG. 6 the normally closed position is shown with the lips 57 in contact with one another to maintain a closed position so long as there is no pressure differential relative to either side of the valve. In FIG. 7, however, when the pressure is no longer equalized, the lips 57 will open, thereby permitting a flow of liquid or air. When the entry of air has equalized the pressure in the present disclosure, the lips 57 will close and the receptacle will assume its normal position or form and be ready for another deformation to inject another flow of liquid via the liquid passageways into the nostril via the occluder 13. It can be readily appreciated that the check valve provides a means for controlling the flow of liquid upon deformation of the pliant receptacle and the direction of flow is only in a direction to discharge the flow from the occluder into the nostril. As described more fully hereinabove, once the pressure has been released from the receptacle, the difference in pressure between the inside and outside of the receptacle causes the check valve 53 in the liquid passageway 51 to close and the check valve 54 in the air passageway 52 to open and remain open until the pressure has been equalized. Through this arrangement any liquid discharged from the occluder into the nostril cannot re-enter the receptacle because of the check valve arrangement. Therefore, any contamination that may have been added to the liquid after it has been dispensed cannot re-enter the receptacle through the occluder 13. Also, with the structure herein provided the structure can be completely disassembled and reassembled for cleaning and disinfecting or sterilizing. Further, at no time is there a possibility of leakage of the liquid from within the receptacle, irrespective of the position of the receptacle.

As set forth hereinabove it can be readily appreciated by anyone skilled in the art that the invention disclosed herein provides a novel way of achieving a result not heretofore possible with presently used dispensers. There may be differences that can be affected without altering the operation, function or purpose of the invention as described and disclosed hereinabove. For example, it has been found that a plastic material is very satisfactory for use as the intermediate member and the occluder inasmuch as such material is easily shaped or molded, light in weight and readily cleaned and sterilized.

Accordingly, the invention has been disclosed in detail with particular reference to preferred embodiments thereof but it will be understood that variations and modifications can be affected within the spirit of the invention.

I claim:

1. A unidirectional liquid dispensing device usable in an upright position for cleaning and flushing the nasal and sinus cavities with a hygienic liquid contained in a pliable receptacle having an open end, the combination comprising:

an intermediate member having a first end extending into the receptacle and releasably attached to the open end for closing and sealing the open end and a second end extending without the receptacle, the intermediate member being provided with a liquid passageway extending from the first end to the second end and an air passageway interconnecting the interior of the receptacle with the atmosphere for normally maintaining the receptacle in a fully extended form;

an occluder releasably attached to the intermediate member at the second end thereof and insertable into one of the nostrils of a nose, the occluder having a liquid discharge end and a liquid passageway coextensive with the discharge end and the liquid passageway of the intermediate member for directing and discharging flow of liquid into the nostril in which the occluder is inserted, and with deformation of the receptacle;

a tubular member having one end releasably attached to the first end of the intermediate member in coextensive relation with the liquid passageway therein and the other end extending into the liquid in the receptacle for providing a continuous interconnecting liquid passageway in conjunction with the aforementioned liquid passageways between the liquid in the receptacle and the discharge end of the occluder;

liquid control means associated with one of the liquid passageways in the intermediate member and the occluder for initiating a unidirectional flow of the liquid, upon deformation of the pliant receptacle, only in a direction for discharge of the liquid from the discharge end of the occluder and into the nostril; and air control means associated with the air passageway for closing the air passageway to the atmosphere, upon deformation of the receptacle, to initiate the flow of the liquid and for preventing reentry of air into the receptacle for reformation of the receptacle only upon concluding the deformation of the receptacle and the flow of the liquid.

2. A device in accordance with claim 1 wherein the liquid control means comprises an anti-retractive check valve arranged within the liquid passageway of the intermediate member for permitting the flow of the liquid only in a direction toward the occluder and preventing the return of any dispensed liquid to the receptacle when deformation of the receptacle is concluded.

3. A device in accordance with claim 1 wherein the liquid control means comprises an anti-retractive check valve arranged within the liquid passageway of the occluder for permitting the flow of the liquid only in a direction toward the discharge end of the occluder when the receptacle is deformed and for preventing the return of any dispensed liquid to the receptacle when deformation of the receptacle is concluded.

* * * * *